United States Patent [19]
Evans

[11] Patent Number: 5,466,228
[45] Date of Patent: Nov. 14, 1995

[54] FLUID CONTROL APPARATUS

[75] Inventor: John M. Evans, Fresno, Calif.

[73] Assignee: California State University, Fresno Foundation, Fresno, Calif.

[21] Appl. No.: 157,647

[22] Filed: Nov. 24, 1993

Related U.S. Application Data

[63] Continuation of Ser. No. 22,606, Feb. 17, 1993, abandoned, which is a continuation of Ser. No. 645,806, Jan. 25, 1991, abandoned.

[51] Int. Cl.[6] ........................................................ A61M 5/00
[52] U.S. Cl. ........................ 604/248; 604/32; 137/625.47
[58] Field of Search ............................ 604/32, 246, 248; 137/625.41, 625.47

[56] References Cited

U.S. PATENT DOCUMENTS

| | | |
|---|---|---|
| 3,048,192 | 8/1962 | Murphy, Jr. . |
| 3,078,848 | 2/1963 | Milbert . |
| 3,678,960 | 7/1972 | Leibinsohn . |
| 3,834,372 | 9/1974 | Turney . |
| 3,927,693 | 12/1975 | Johnston . |
| 4,775,365 | 10/1988 | Swartz . |
| 4,819,694 | 4/1989 | Jiang . |
| 4,904,245 | 2/1990 | Chen et al. .............................. 604/248 |

*Primary Examiner*—Corrine M. Maglione
*Attorney, Agent, or Firm*—Worrel & Worrel

[57] ABSTRACT

A fluid control apparatus comprising a housing having a plurality of discrete ports; conduits individually interconnecting the ports and discrete sources of, and receptacles for, fluid; and a valve member positionable in the housing in preselected fluid transferring positions relative to said ports whereby, in a first fluid transferring position, fluid can be transferred by the valve member from one of the fluid sources to one of the fluid receptacles through the ports thereof and, in a second fluid transferring position, fluid can be transferred by the valve member from the one of the fluid receptacles to a second of the fluid receptacles through the ports.

6 Claims, 2 Drawing Sheets

FLUID CONTROL APPARATUS

This is a continuation of application Ser. No. 08/022,606, filed on Feb. 17, 1993 now abandoned, which is a continuation of Ser. No. 07/645,806, filed Jan. 25, 1991 now abandoned.

BACKGROUND OF THE INVENTION

1. Field of the Invention

The present invention relates to a fluid control apparatus and, more particularly, to a fluid control apparatus which is operable to transfer fluids along discrete paths of travel among a plurality of sources of and receptacles for fluid pursuant to a preconceived sequence of steps for a multiplicity of predetermined operational objectives.

2. Description of the Prior Art

A multitude of environments exist within which it is necessary or desirable sequentially to direct one or more fluids along discrete paths of travel to accomplish specific operational objectives. In many such environments, it is both necessary and desirable to perform these operations in such a fashion that the fluids are isolated from human contact. Still further, these operations must typically be performed rapidly, but with a precision guaranteeing that all of the operational objectives are achieved in a fully sanitary environment.

There are a variety of medical procedures which require that these criteria be met. For example, it is common to employ gastric irrigations, bladder irrigations, and the like for the therapeutic treatment of injured or diseased tissues. For such procedures, any of a wide variety of therapeutic solutions are directed into the affected organ, in some cases allowed to remain for a prescribed period of time and removed therefrom for collection in a container for subsequent examination and/or disposal. It has, heretofore, been exceedingly difficult to perform these procedures dependably, expeditiously and without the risk of contamination of the patient, medical personnel or the environment. Furthermore, since prior art equipment employed for the purpose is typically clumsy, difficult to operate and thereby frustrating to use, such prior art devices are frequently improperly operated creating a risk of injury to the patient, in effective administration of the treatment, contamination and the like.

While there have in the past been attempts to develop a fluid control device which was fully capable of performing all of the criteria required of such procedures without the myriad of problems heretofore associated therewith, insofar as the applicant is aware, all such prior art attempts have failed to produce the desired results.

Therefore, it has long been known that it would be desirable to have a fluid control apparatus which is selectively operable to direct one or more fluids along predetermined discrete paths of travel among selected sources of, and receptacles for, such fluid in a predetermined sequence of steps, which is capable of performing the sequence of steps in any sequence prescribed therefor, which is operable to perform such operations expeditiously and dependably without risk of inadvertent operation and which performs these functions without risk of contamination to those involved in the operation or to the environment.

SUMMARY OF THE INVENTION

Therefore, it is an object of the present invention to provide an improved fluid control apparatus.

Another object is to provide such a fluid control apparatus which is operable to direct one or more fluids along discrete paths of travel fully within the control of the operator thereof.

Another object is to provide such a fluid control apparatus which can be employed to direct fluids along preselected courses in complete isolation from the operator thereof so as to avoid fluid loss or release into the environment.

Another object is to provide such a fluid control apparatus which has a plurality of ports any two, but not more, of which can be interconnected completely within the control of and at the discretion of the operator thereof.

Another object is to provide such a fluid control apparatus which is of both convenient and uncomplicated operation thereby avoiding the risk of inadvertent operation.

Another object is to provide such a fluid control apparatus which is particularly well suited to use in a wide variety of medical procedures, including for example gastric and bladder irrigations, permitting both gravity and pressure operation, permitting therapeutic solutions to be applied and their use fully controlled at the discretion of the operator.

Another object is to provide such a fluid control apparatus which is fully compatible in use with conventional appliances employed in all of the medical procedures to which it has application.

Further objects and advantages are to provide improved elements and arrangements thereof in an apparatus for the purpose described which is dependable, economical, durable and fully effective in accomplishing its intended purpose.

These and other objects and advantages are achieved, in the preferred embodiment of the apparatus of the present invention in a fluid control apparatus, having a housing with a plurality of discrete ports; means for individually interconnecting the ports and discrete sources of, and receptacles for, fluid; and a valve member positionable in the housing in preselected fluid transferring positions relative to the ports whereby, in a first fluid transferring position, fluid can be transferred by the valve member from one of the fluid sources to one of the fluid receptacles through the ports thereof and, in a second fluid transferring position, fluid can be transferred by the valve member from the one of the fluid receptacles to a second of the fluid receptacles through the ports thereof.

DESCRIPTION OF THE PREFERRED EMBODIMENT

Figure 1:
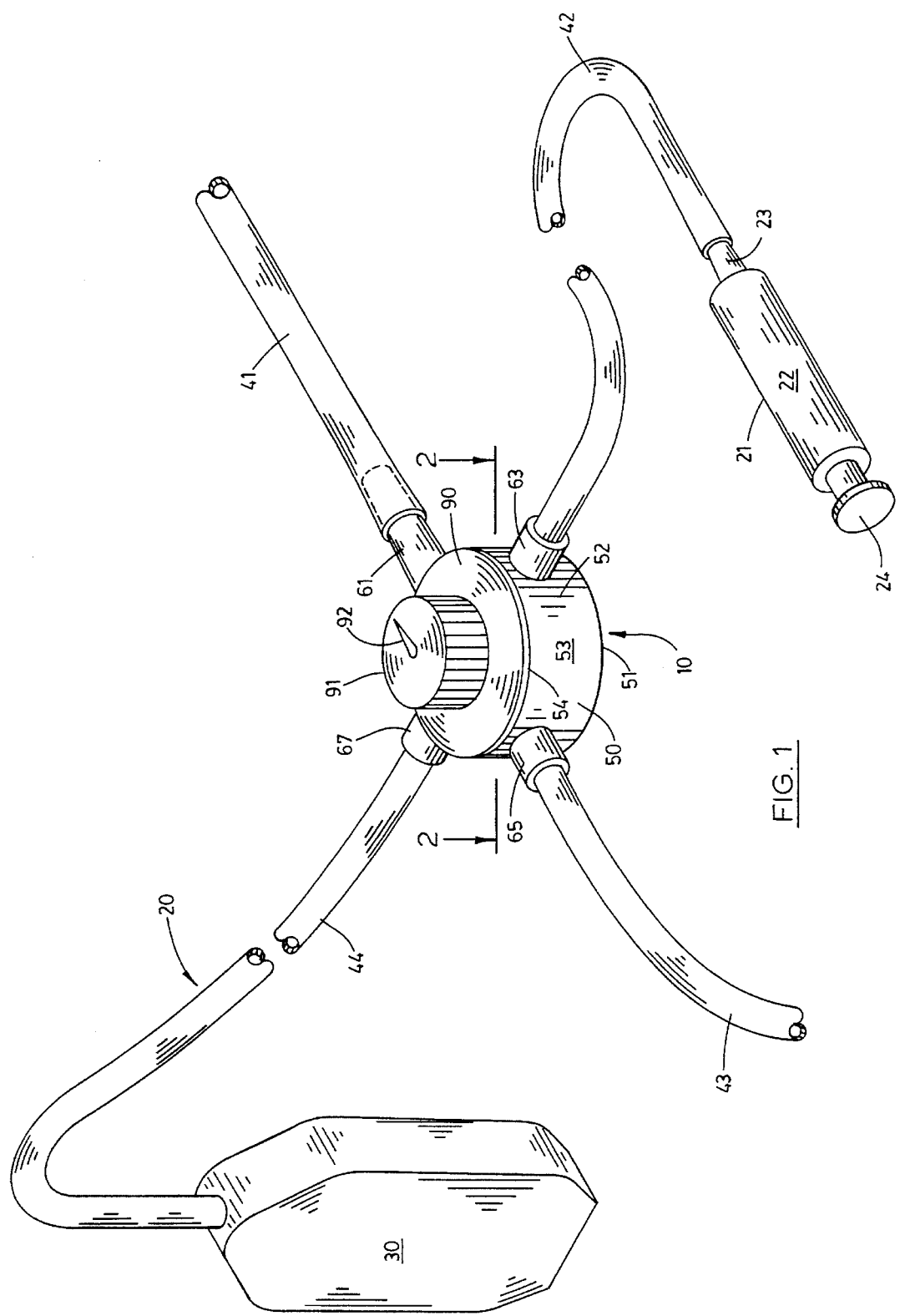
FIG. 1 is a fragmentary, perspective view showing the fluid control apparatus of the present invention in a typical operative environment, that being mounted as an operable part of a patient irrigation assembly.

The fluid control apparatus of the present invention is generally indicated by the numeral 10 in FIG. 1. The fluid control apparatus can be employed in a host of different operative environments, including any environment in which it is necessary to control the flow of one or more fluids between two or more sources and receptacles thereof. However, the fluid control apparatus is particularly well suited to usage in the performance of a wide variety of medical procedures where such fluid control is necessary or desirable. Examples of these include gastric irrigations, bladder irrigations, internal feedings, wound irrigations and the like.

In the operative environment of FIG. 1, a patient irrigation assembly is generally indicated by the numeral 20. The irrigation assembly shown for illustrative convenience may be considered that adapted for the performance of gastric or bladder irrigations.

As shown in FIG. 1, a conventional syringe 21 has a cylindrical housing 22 having a head portion 23 and a plunger 24.

The patient irrigation assembly 20 includes a drainage collection receptacle 30 of any suitable type. The patient irrigation assembly further includes a first conduit 41 adapted to extend to a patient, not shown. For purposes of understanding in the illustrative embodiment, the first conduit 41 may be considered to be a conduit extending into the stomach of the patient through the nose or mouth, or a conduit extending into the bladder of the patient for purposes of bladder irrigation. Patient irrigation assembly further includes a second conduit 42 which is, as shown in FIG. 1, extended over the head portion 23 of the syringe 21 in fluid communicating relation. The patient irrigation assembly includes a third conduit 43 which extends to a suitable source, not shown, of the fluid or solution employed in the irrigation procedure. A fourth conduit 44 is connected in fluid transferring relation to the drainage collection receptacle 30.

The fluid control apparatus 10 of the present invention has a housing 50 which can be constructed of any suitable material such as, for example, injection molded polyethylene. The housing has a bottom wall 51 having a cylindrical side wall 52 extending upwardly therefrom concentric to a longitudinal axis, not shown. The cylindrical side wall has a cylindrical exterior surface 53 and an annular upper edge 54. The cylindrical side wall has a cylindrical interior surface 55 bounding an interior chamber 56 of the housing.

A tapered conduit sleeve 61 is mounted on and is integral with the cylindrical side wall 52 of the housing 50. A tapered conduit sleeve bounds a first housing port 62. A cylindrical conduit sleeve 63 is mounted on and is integral with the cylindrical side wall on the right as viewed in FIGS. 2A through 2F. The cylindrical conduit sleeve 63 bounds a second housing port 64. A cylindrical conduit sleeve 65 is mounted on and is integral with the cylindrical side wall bounding a third housing port 66 directly 180 degrees (180°) opposite the first housing port 62. A cylindrical conduit sleeve 67 is mounted on and is integral with the cylindrical side wall on the left as viewed in FIGS. 2A through 2F and bounds a fourth housing port 68.

Figure 2C:
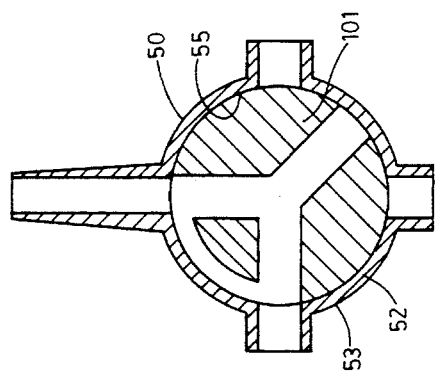
FIG. 2C is a horizontal section taken from a position indicated by line 2—2 in FIG. 1 and showing the valve member in a second fluid transferring position.
Figure 2F:
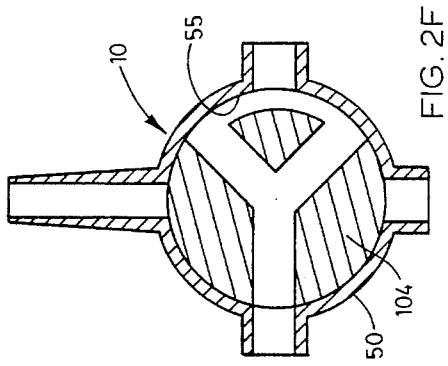
FIG. 2F is a horizontal section taken from a position indicated by line 2—2 in FIG. 1 and showing the valve member in a fifth fluid transferring position.
Figure 2B:
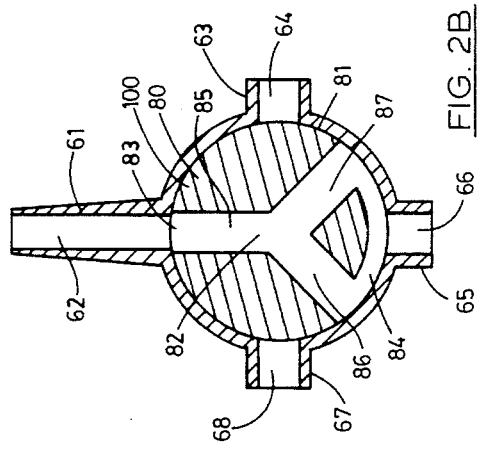
FIG. 2B is a horizontal section taken from a position indicated by line 2—2 in FIG. 1 and showing the valve member in a first fluid transferring position.
Figure 2E:
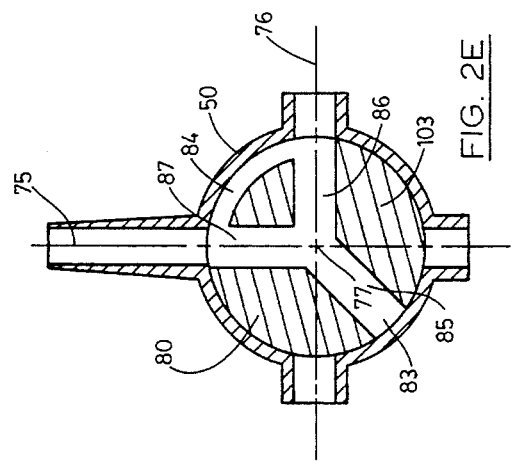
FIG. 2E is a horizontal section taken from a position indicated by line 2—2 in FIG. 1 and showing the valve member in a fourth fluid transferring position.
Figure 2A:
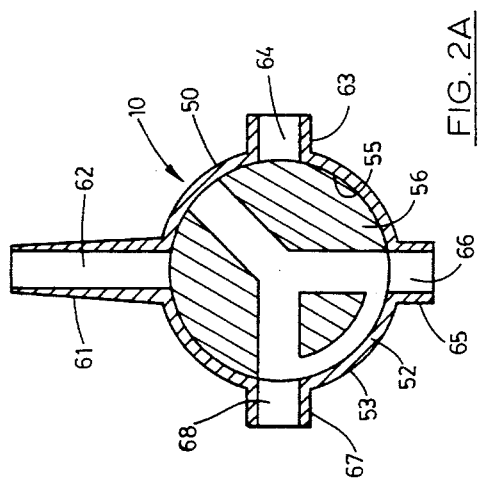
FIG. 2A is a horizontal section of the fluid control apparatus taken from a position indicated by line 2—2 in FIG. 1 and showing the valve member thereof in a position such as to interconnect a third port with a fourth port of the housing of the fluid control apparatus.

As can best be visualized in FIG. 2E, the first housing port 62 and the third housing port 66 are aligned along a longitudinal axis 75. Similarly, the second housing port 64 and the fourth port 68 are aligned along a longitudinal axis 76. The longitudinal axes 75 and 76 intersect each other at substantially right angles at reference point 77 which is coextensive with the longitudinal axis of the cylindrical side wall 52 of the housing 50 and defines a plane at right angles thereto.

A valve member 80 is mounted for rotational movement in the interior chamber 56 of the housing 50. The valve member is mounted for such rotational movement by any suitable means including simply being captured within the interior chamber or by any other suitable means. The valve member, in the preferred embodiment, is constructed of injection molded "Lexan PC HP$_1$". The valve member 80 has an outer cylindrical surface 81 which facingly engages the interior surface 55 of the cylindrical side wall 52. A valve passage 82 extends through the valve member communicating with the exterior of the valve member at the outer cylindrical surface through a first valve port 83 having a substantially circular configuration. The valve passage communicates with the exterior of the valve member on the opposite side thereof through an elongated second valve port 84 extending more than 90 degrees (90°) about the outer cylindrical surface 81. The first valve port and the second valve port are interconnected in the valve passage by a first passage section 85 extending from the first valve port 83 inwardly of the valve member. A second passage section 86 and a third passage section 87 individually extend inwardly of the valve member from the opposite ends of the elongated second valve port substantially at right angles to each other. Thus, the first, second and third passage sections join each other centrally of the valve member coincident with the reference point 77.

The housing 50 has a housing closure 90 secured by any suitable means on the annular upper edge 54 of the cylindrical side wall 52 capturing the valve member 80 within the interior chamber 56 of the housing in fluid tight relation. A control member 91 is mounted on the valve member 80 by any suitable means, not shown, such as by a shaft extending from the control member through the housing closure and mounted on the valve member. The control member is mounted for rotation with the valve member about a common longitudinal axis coincident with the reference point 77 and the longitudinal axis of the cylindrical side wall 52. Suitable indicia 92 are provided on the control member who indicate the position of the valve passage 82 relative to the housing.

Referring more particularly to FIGS. 2B through 2F, a number of fluid transferring positions for the valve member 80 are shown therein, as will hereinafter be described in greater detail. A first fluid transferring position is indicated at 100 in FIG. 2B. A second fluid transferring position is indicated at 101 in FIG. 2C. A third fluid transferring position is indicated at 102 in FIG. 2D. A fourth fluid transferring position is indicated at 103 in FIG. 2E. A fifth fluid transferring position is indicated at 104 in FIG. 2F.

OPERATION

The operation of the described embodiment of the subject invention is believed to be clearly apparent and is briefly summarized at this point. While, as previously noted, the fluid control apparatus of the present invention can be employed in a wide variety of environments, the illustrative environment heretofore described, when used in combination with the patient irrigation assembly 20, has particular utility. When so used, the patient irrigation assembly 20 can be operated by two distinct general methods.

The first general method of operation of the patient irrigation assembly 20 is illustrated in FIGS. 2B and 2C to perform the irrigation operation by gravity flow. Using the control member 91, and as indicated by the indicia 92, the valve member 80 is moved to the first fluid transferring position 100 shown in FIG. 2B. As can be seen therein, this position interconnects the first housing port 62 and third housing port 66 in fluid transferring relation through the valve passage 82. The medical procedure is then preformed by raising the source, not shown, of fluid connected to third conduit 43 to cause the fluid to flow by gravity through conduit 43, third housing port 66, valve passage 82, first housing port 62, and through the first conduit 41 into the patient.

This procedure is preformed in the desired fashion using conventional medical techniques until it is desired to drain the fluid from the patient. Since the irrigation fluid is contaminated with blood, body secretions find other contaminants, it is necessary safely to collect the drainage for disposal, or in some cases for laboratory examination. Thus, before the patient irrigation assembly 20 is lowered to allow the fluid to drain by gravity back into the system, the valve member 80 is moved to the second fluid transferring position 101 shown in FIG. 2C using the control member 91. As can be seen by reference to FIG. 2C, this causes the first housing port 62 and fourth housing port 68 to be interconnected by the valve passage through the second passage section 86 and third passage section 87 as well as by the arcuate area constituting a portion of the elongated second valve port between the interior surface 55 of the cylindrical side wall 52 of the housing 50 and the valve member. The patient irrigation assembly 20 is then again lowered to allow the fluid to drain from the patient along first conduit 41 valve passage 82 of the valve member 80, fourth conduit 44 and into the drainage collection receptacle 30.

Figure 2D:
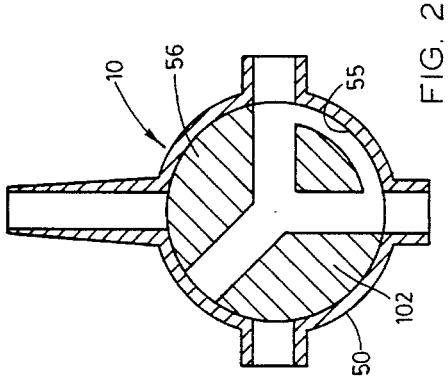
FIG. 2D is a horizontal section taken from a position indicated by line 2—2 in FIG. 1 and showing the valve member in a third fluid transferring position.

The subject medical procedure for irrigation of the illustrative environment can also be performed, using the fluid control apparatus 10 of the present invention in combination with the patient irrigation assembly 20, by pressure in addition to, or other than, gravity. The sequence of steps for performing the medical procedure in this manner is shown in FIGS. 2D through 2F. The head portion 23 of the syringe 21 is inserted in the second conduit 42 as shown in FIG. 1. The cylindrical housing 22 of the syringe is at this time empty and the plunger 24 is in the retracted position shown in FIG. 1. The valve member 80 is moved to the third fluid transferring position 102 shown in FIG. 2D. As can be seen in FIG. 2D, this position interconnects the third conduit 43, and thus the source of treating fluid, not shown, and the second conduit 42, and thus the syringe 21. By raising the source of fluid connected to the third conduit 43, the treating fluid flows through the third conduit 43, through the valve passage 82, and into the second conduit 42. Upon the fluid reaching the syringe, the operator withdraws the plunger 24 thereof to draw the treating fluid into the cylindrical housing 22 of the syringe. The valve member is then moved to the fourth fluid transferring position, shown in FIG. 2E, thereby interconnecting the second conduit 42 with the first conduit 41. The plunger 24 of the syringe is then pushed inwardly of the housing to the retracted position, shown in FIG. 1, to force the treating fluid from the syringe, through the second conduit 42, through the valve passage 82 of the valve member, through the first conduit 41 and into the patient.

Once the medical procedure has performed its function, and with the valve member in the fourth fluid transferring position 103, shown in FIG. 2E, the plunger 24 of the syringe is again withdrawn from the retracted position, shown in FIG. 1, to an extended position vacuumatically to draw the treating fluid and its contents back into the cylindrical housing 22 of the syringe.

Subsequently, the valve member 80 is moved to the fifth fluid transferring position 104, shown in FIG. 2F. When this has been achieved, the operator again depresses the plunger 24 of the syringe 21 to force the treating fluid from the cylindrical housing 22 of the syringe along the second conduit 42, through the valve passage 82, through the fourth conduit 44 and into the drainage collection receptacle 30.

All of the operations heretofore described using the fluid control apparatus 10 of the present invention, in the illustrative environment with the patient irrigation assembly 20, are achieved rapidly, dependably and with all of the fluids completely isolated from the patient, hospital personnel and the environment. Due to the simplicity of its structure and operation, the fluid control apparatus possesses substantially no opportunity for inadvertent operation. Similarly, the structure of the fluid control apparatus 10 is such that the fluid control apparatus can be manufactured at nominal expense and operated over a long operational life without failure. Still further, as heretofore noted, the fluid control apparatus is adaptable for use in almost any environment in which it is necessary to move fluids along discrete courses in a sequence of steps under the control of an operator.

Therefore, the fluid control apparatus of the present invention provides a precise and dependable means by which one or more fluids can be transported along discrete courses selected by the operator possessing a multiplicity of possible fluid transferring positions adaptable for even the most complex treating operations with little or no risk of inadvertent operation or contamination of the environment or those in the vicinity.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by letters patent is:

1. A fluid control apparatus for interconnecting at any one time any two, but not more than two, of a plurality of individual sources of fluid and receptacles for fluid, the fluid control apparatus comprising a housing having a wall enclosing a substantially cylindrical interior substantially concentric to a longitudinal axis and having four housing ports extending through the wall and communicating with the interior of the housing, said housing ports spaced from each other ninety degrees (90°) about the wall relative to said longitudinal axis so that each of said housing ports is in axial alignment with a housing port on the opposite side of the housing through said interior thereof; means for individually connecting each of said housing ports to one of the sources of fluid or receptacles for fluid; and a valve member mounted in said interior of the housing for movement therewithin substantially about said longitudinal axis and having a substantially cylindrical external surface disposed in facing engagement with said wall of the housing, a first valve port, individually positionable in fluid transferring relation with each of said housing ports, an elongated second valve port, extending approximately ninety degrees (90°) about the periphery of the valve member to opposite ends and disposed on the opposite side of the valve member from said first valve port, and a passage extending through the valve member interconnecting the first valve port and the second valve port and wherein said passage has a "Y" shaped configuration having two portions thereof disposed at a right angle to each other interconnecting the opposite ends of the second valve port whereby said valve member can selectively be positioned in a plurality of fluid transferring positions but in each of said fluid transferring positions can connect only two of said four housing ports at any one time through the passage thereof.

2. The fluid control apparatus of claim 1 wherein said passage includes three sections thereof individually extending from said first valve port and from both ends of said second valve port inwardly of the valve member and intersecting with each other substantially coincident with said longitudinal axis.

3. The fluid control apparatus of claim 2 wherein said sections of the passage extending from both ends of said second valve port are disposed substantially at right angles to each other.

4. The fluid control apparatus of claim 3 wherein said housing has a closure overlaying the valve member in substantially fluid sealing relation and a control member is mounted externally of said closure and has a portion extending through the closure connected to said valve member whereby the valve member is selectively positionable in said fluid transferring positions using the control member.

5. The fluid control apparatus of claim 1 wherein the fluid control apparatus is to be employed with a patient and a syringe, wherein said individual connecting means includes a first conduit interconnecting a first of said four housing ports and the patient, a second conduit interconnecting a second of said four housing ports and the syringe, a third conduit interconnecting a third of said four housing ports and a source of irrigating fluid and a fourth conduit interconnecting a fourth of said four housing ports and a fluid receptacle whereby said valve member can be moved to a first fluid transferring position interconnecting the third conduit and the first conduit to permit irrigating fluid to pass through the valve member from the source of irrigating fluid to the patient, the valve member can subsequently be moved to a second fluid transferring position interconnecting the first conduit and the fourth conduit to permit irrigating fluid to pass through the valve member from the patient into the fluid receptacle.

6. The fluid control apparatus of claim 5 wherein the valve member can be moved to a third fluid transferring position interconnecting the third conduit and the second conduit to permit irrigating fluid to be drawn into the syringe through the valve member from the source of irrigating fluid, the valve member can subsequently be moved to a fourth fluid transferring position interconnecting the second conduit and the first conduit through the valve member to permit the irrigating fluid to be forced from the syringe to the patient and subsequently drawn by the syringe back into the syringe from the patient through the valve member and the valve member can subsequently be moved to a fifth fluid transferring position interconnecting the second conduit and the fourth conduit through the valve member permitting the irrigating fluid to be forced by the syringe through the valve member into the fluid receptacle.

* * * * *

UNITED STATES PATENT AND TRADEMARK OFFICE
CERTIFICATE OF CORRECTION

PATENT NO. : 5,466,228

DATED : November 14, 1995

INVENTOR(S) : John M. Evans

It is certified that error appears in the above-identified patent and that said Letters Patent is hereby corrected as shown below:

```
Column 4, line 6, between "fourth" and "port"
     insert ---housing---.

Column 5, line 24, delete "find" and substitute
                   ---and---.
```

Signed and Sealed this

Twenty-sixth Day of March, 1996

Attest:

BRUCE LEHMAN

*Attesting Officer*  *Commissioner of Patents and Trademarks*